United States Patent

Albright

[11] 4,099,975
[45] * Jul. 11, 1978

[54] INTUMESCENT FIRE RETARDANT COMPOSITIONS CONTAINING PENTAERYTHRITOL CYCLIC DIPHOSPHATES

[75] Inventor: James A. Albright, Ann Arbor, Mich.

[73] Assignee: Velsicol Chemical Corporation, Chicago, Ill.

[*] Notice: The portion of the term of this patent subsequent to Dec. 14, 1993, has been disclaimed.

[21] Appl. No.: 650,282

[22] Filed: Jan. 19, 1976

Related U.S. Application Data

[63] Continuation-in-part of Ser. No. 616,935, Sep. 26, 1975, Pat. No. 3,978,167, which is a continuation-in-part of Ser. No. 429,607, Jan. 2, 1974, abandoned.

[51] Int. Cl.² ............................................. C08K 5/53
[52] U.S. Cl. .......................... 106/15 FP; 260/45.8 R
[58] Field of Search ............... 260/45.8 R; 106/15 FP

[56] References Cited

U.S. PATENT DOCUMENTS

| | | | |
|---|---|---|---|
| 3,090,799 | 12/1963 | Wahl et al. ........................ | 260/927 R |
| 3,584,085 | 6/1971 | Hartmann ............................ | 260/959 |
| 3,645,971 | 2/1972 | Hindersinn ........................... | 260/830 |
| 3,810,838 | 5/1974 | Haugen ................................ | 260/959 |
| 3,866,405 | 2/1975 | Knopka .................................. | 260/47 |
| 3,997,505 | 12/1976 | Albright .......................... | 260/45.8 R |

Primary Examiner—V. P. Hoke
Attorney, Agent, or Firm—Robert M. Phipps; Howard J. Greenwald

[57] ABSTRACT

Intumescent coating compositions comprising a coating vehicle and a non-flaming intumescent agent of the formula

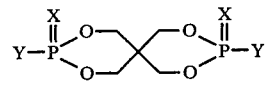

wherein both X's are identical and selected from the group comprising oxygen and sulfur and wherein each Y is independently selected from the group consisting of alkoxy, halogenated alkoxy, cycloalkoxy, halogenated cycloalkoxy, olefinicoxy, halogenated olefinicoxy and —NR₂ groups, wherein each R is independently selected from the group consisting of hydrogen, alkyl, halogenated alkyl, olefinic, and halogenated olefinic groups, said alkoxy, cycloalkoxy, olefinicoxy, alkyl and olefinic groups containing from 1 to about 12 carbon atoms and said halogenated groups containing from 1 to about 6 halogen substituents per group. A method for protecting a substrate from heat and fire comprising applying to the substrate an intumescing amount of the above described intumescent agents.

9 Claims, No Drawings

INTUMESCENT FIRE RETARDANT COMPOSITIONS CONTAINING PENTAERYTHRITOL CYCLIC DIPHOSPHATES

RELATED PATENT APPLICATIONS

This application is a continuation-in-part of copending application, Ser. No. 616,935, filed Sept. 26, 1975, now U.S. Pat. No. 3,978,167, which in turn is a continuation-in-part of copending application, Ser. No. 429,607, filed Jan. 2, 1974, and now forfeited.

BACKGROUND OF THE INVENTION

1. Field of the Invention

This invention pertains to an intumescent composition comprising a polymer and a non-flaming, phosphorus-containing intumescent preservative agent.

2. Description of the Prior Art

It is known that a substrate may be protected from heat and fire by the application of an intumescent composition. Intumescent compositions of the prior art usually contain an intumescent agent having at least three components, i.e., a carbonific, a spumific, and a catalyst; and they are typically characterized by the disadvantages of high cost, low spreading rate, relatively poor efficiency, poor water resistance, and poor weatherability.

As disclosed in U.S. Pat. No. 3,535,130, it has been discovered that a one-component intumescent agent has advantages over multicomponent intumescent agents. However, the intumescent agents of said patent are reported to have poor adherence to substrates and have an undesirable degree of moisture sensitivity, see U.S. Pat. No. 3,855,134.

Other one-component intumescent agents stated as having good efficiency, a low level of moisture sensitivity, and good adherence to substrates are reported in U.S. Pat. No. 3,855,134. However, many of these new intumescent agents intumesce with a slight self-extinguishing flame which makes them less desirable for applications having very stringent requirements. Therefore, U.S. Pat. No. 3,855,134 discloses a method for combining said new intumescent agents with halo-organophosphorus compounds to render the normally self-extinguishing intumescent agents non-flaming.

This application is directed to one-compound intumescent agents having good efficiency, excellent hydrolytic stability, good adherence to substrates, and possessing inherent non-flaming intumescent characteristics.

SUMMARY OF THE INVENTION

Disclosed in an intumescent composition comprising a coating vehicle and a non-flaming intumescent agent of the formula

(I)

wherein both X's are identical and selected from the group comprising oxygen and sulfur and wherein each Y is independently selected from the group consisting of alkoxy, halogenated alkoxy, cycloalkoxy, halogenated cycloalkoxy, olefinicoxy, halogenated olefinicoxy and —NR$_2$ groups, wherein each R is independently selected from the group consisting of hydrogen, alkyl, halogenated alkyl, olefinic, and halogenated olefinic groups, said alkoxy, cycloalkoxy, olefinicoxy, alkyl, and olefinic groups containing from 1 to about 12 carbon atoms, and said halogenated groups containing from 1 about 6 halogen substituents per group. A method for protecting a substrate from heat and fire comprising applying to said substrate an intumescing amount of the above described intumescent agents is also included within the scope of this invention.

DESCRIPTION OF THE PREFERRED EMBODIMENTS

The compounds of the above formula I include both the cyclic diphosphate esters and the cyclic diphosphoramidates of pentaerythritol. The compounds can also be generically described as 3,9-substituted-2,4,8,10-tetraoxa-3,9-diphosphaspiro(5.5)undecane-3,9-dioxides or disulfides.

As indicated by the generic formula, the X groups attached to the phosphorus atoms can be either sulfur or oxygen. Oxygen is the preferred substituent for most compounds included herein.

Each Y is independently selected from the group consisting of alkoxy, halogenated alkoxy, cycloalkoxy, halogenated cycloalkoxy, olefinicoxy, halogenated olefinicoxy, and —NR$_2$ groups, wherein each R is independently selected from the group consisting of hydrogen, alkyl, halogenated alkyl, olefinic, and halogenated olefinic groups. Preferably, each Y is independently selected from the group consisting of alkoxy, halogenated alkoxy, and —NR$_2$ groups, wherein each R is independently selected from the group consisting of hydrogen, alkyl, and halogenated alkyl groups. It is also preferred that both Y's be identical. The alkoxy, cycloalkoxy, olefinicoxy, alkyl, and olefinic groups contain from 1 to about 12 carbon atoms, preferably from 1 to about 6 carbon atoms, per group. The alkoxy, olefinicoxy, alkyl, and olefinic groups can be straight or branched chain groups. The halogenated groups contain from 1 to about 6, preferably from 1 to about 3, halogen substituents per group. The halogen atoms present on the halogenated groups are selected from the group comprising fluorine, chlorine, bromine, and iodine. Of the foregoing, chlorine and bromine are preferred. Examples of suitable halogenated alkoxy, cycloalkoxy, olefinoxy, alkyl, and olefinic groups include bromoethoxy, dibromoethoxy, dibromopropoxy, dibromobutadieneoxy, tribromobutoxy, dichlorocyclohexoxy, dichlorobromocyclohexoxy, chlorodibromopropoxy, chlorodibromoneopentyloxy, difluorochlorethoxy, bromoiododopropoxy, difluorochlorohexoxy, dichlorohexabromoidodohexeneoxy, iodoethoxy, chloropentabromocyclohexoxy, fluorohexabromobutoxy, tetrafluorocyclobutoxy, diiodobuteneoxy, difluoroallyloxy, dibromodichlorohexeneoxy, dibromopropyl, dibromobutadienyl and the like.

Examples of suitable amino groups include amino, diethylamino, propylamino, methylamino, dimethylamino, chloromethylamino, di(chloroethyl)amino, di(tribromochloroethyl)amino, di(dichlorobromoisopropyl)amino, diallylamino, di(diiodoethyl)amino and bis(2,3-dibromopropyl)amino.

The pentaerythritol cyclic diphosphate and diphosphoramidate intumescent agents within the scope of this invention both possess excellent hydrolytic stability. However, when the intumescent agent being used is a pentaerythritol cyclic diphosphate and the intumescent agent's hydrolytic stability is of the essence, it is preferred that the Y groups of said pentaerythritol cyclic diphosphate each be

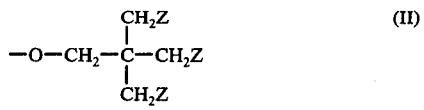

wherein each Z is independently selected from the group consisting of hydrogen, fluorine, chlorine, bromine, and iodine, preferably hydrogen, chlorine, and bromine, and more preferably chlorine and bromine. Examples of suitable groups of the above neopentyloxy structure are listed in Table I. Table I is for purposes of illustration only and is not to be construed as a limitation on the scope of this invention. The following is a partial listing of those preferred compounds which have the above neopentyloxy moiety: 3,9-bis(2,2-(dibromomethyl)-3-bromopropoxy)-2,4,8,10-tetraoxa-3,9-diphosphaspiro(5.5)undecane-3,9-dioxide, 3,9-bis(2,2-(dichloromethyl)-3-chloropropoxy)-2,4,8,10-tetraoxa-3,9-diphosphaspiro(5.5)-undecane-3,9-dioxide, 3,9-bis(2,2-(dimethyl)-3-chloropropoxy)-2,4,-8,10-tetraoxa-3,9-diphosphaspiro(5.5) undecane-3,9-dioxide, 3,9-bis-(2,2-(dimethyl)-3-bromopropoxy)-2,4,8,10-tetraoxa-3,9-diphosphaspiro(5.5)undecane-3,9-dioxide, 3,9-bis(2,2-(dibromomethyl)-3-chloropropoxy-2,4,8,10-tetraoxa-3,9-diphosphaspiro(5.5)undecane-3,9-dioxide, 3,9-bis(2,2-(dichloromethyl)-3-bromopropoxy)-2,4,8,10-tetraoxa-3,9-diphosphaspiro(5.5)undecane-3,9-dioxide, and 3,9-bis(2,2-dimethylpropoxy)-2,4,8,10-tetraoxa-3,9-diphosphaspiro(5.5)undecane-3,9-dioxide.

TABLE I

| Group | Z | Z | Z |
|---|---|---|---|
| 1 | Br | Br | Br |
| 2 | Cl | Cl | Cl |
| 3 | H | H | Cl |
| 4 | H | H | Br |
| 5 | Br | Cl | Br |
| 6 | Cl | Br | Cl |
| 7 | H | H | H |

All of the aforedescribed and aforementioned Y groups can be attached to the diphosphoryl or dithiophosphoryl pentaerythritol group, also characterized as 3,9-substituted-2,4,8,10-tetraoxa-3,9-diphosphaspiro(5.5)undecane-3,9-dioxide or disulfide. The numerical designation used in naming the compounds of this invention can be ascertained by reference to the following formula where the members of the heterocyclic rings are numbered.

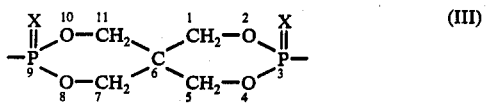

Two representative compounds are 3,9-bis(2,3,-dibromopropoxy)-2,4,-8,10-tetraoxa-3,9-diphosphaspiro(5.5)undecane-3,9-dioxide and 3,9-bis(N,N-diethylamino)-2,4,8,10-tetraoxa-3,9-diphosphaspiro(5.5)-undecane-3,9-dioxide. Two additional representative compounds are the 3,9-disulfide analogs of the above two compounds.

In addition to the 3,9-bis-substituted compounds, an even larger number of 3,9-substituted compounds where the 3- and 9-substituents are different from each other are also included within the scope of this invention. The substituents can be varied to produce mixed diphosphate esters, mixed diphoshoramidates and combination phosphate - phoshoramidate compounds. Exemplary combinations of 3- and 9-substituents include dibromoethoxy and tribromochlorobutoxy; dibromopropoxy and dibromochloroneopentyloxy; bromoethylamino and dibromochlorobutoxy; diethylamino and dibromopropoxy; and unsubstituted amino and diiodoisopropoxy.

The compounds of the present invention can be prepared by reacting a 3,9-dihalo-2,4,8,10-tetraoxa-3,9-diphosphaspiro(5.5)-undecane-3,9-dioxide or disulfide with an alcohol or an amine to yield the appropriate diphosphate ester or diphosphoroamidate. The equation for the reaction is:

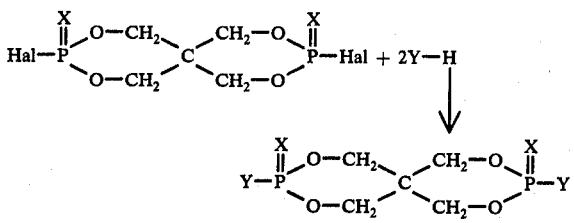

where Y has the meaning set forth above in the description of the compounds and where Hal indicates a halogen atom. As an alternative reactant for the alcohol or amine, the metal salts of the alcohol or amine can be used. If it is desired that the two Y groups be different from each other, two different Y—H reactants should be employed. The reaction can be carried out by simply mixing the halophosphate and the alcohol or amine reactants together and heating the mixture gently for a period of time. In addition, the reaction can be conducted in the presence of an inert solvent, for example, ethylene dichloride or aromatic solvents such as benzene and toluene. The conditions of reaction will vary widely depending upon the reactants, but heating the reactants under gentle refluxing conditions for a period of time of up to 3 or 4 hours is acceptable for preparing many of the compounds of this invention. Catalytic quantities of a metal salt or oxide such as magnesium oxide, magnesium chloride, calcium oxide, calcium chloride, titanium chloride or vanadium acetate, or stoichiometric quantities of a weak organic base such as pyridine or triethylamine, can be used to accelerate the completion of the reaction. The halophosphate starting reaction can be prepared by reacting pentaerythritol with phosphorus oxyhalide.

For use in protecting a substrate from heat and fire, the nonflaming intumescent agents of this invention may be applied in any suitable manner to a desired substrate. However, it is usually preferred to apply said non-flaming intumescent agents via an intumescent coating composition comprising a coating vehicle and said intumescent agent or mixture of intumescent agents. For example, the intumescent agent can be compounded with a binder coating vehicle, e.g., alkyd type surface coating, and optionally also with one or more of the other ingredients conventionally used in intumescent compositions, e.g., stabilizers, dispersing agents, pigments, dryers, biocides, anti-foamers, thickeners, protective colloids, fillers, blowing agents, etc. Alternatively, the non-flaming intumescent agent can be dispersed in a suitable liquid medium coating vehicle, e.g., water or a solvent or solvent mixtures. The intumescent coating composition thus formed can be applied to the substrate to be protected. As in the case with conventional intumescent coating compositions, it is frequently convenient to apply these coating compositions in the form of a paint having a solids content of about 10 to about 70 percent by weight and an intumescent agent-/binder weight ratio of about 0.075 to 14/1 to deposit a coating having a dry thickness of about 0.001 to about 0.75 inch. A further description of the paints, oils, resins, varnishes, polymers, lacquers, etc., as well as the stabilizers, dispersing agents, pigments, dryers, biocides, anti-foamers, thickeners, protective colloids, fillers, blowing agents, etc., all of which can form the coating vehicle with which the non-flaming intumescent agents of formula I can be combined to form this invention's intumescent coating compositions may be found in E. Singer, Fundamentals of Paint, Varnish, and Lacquer Technology, The American Paint Journal Company, St. Louis, Mo. (1957), J. J. Mattiello, Protective and Decorative Coatings, Vols. I through V. John Wiley & Sons, Inc., New York, N.Y. (1941), M. W. Ranney, Fire Retardant Building Products and Coatings 1970, Noyes Data Corp., Park Ridge, N.J. (1970), H. L. Vandersall, Intumescent Coating Systems, Their Development and Chemistry, Journal of Fire and Flammability, 2, 97 (1971), H. F. Payne, Organic Coating Technology, Vol. 1, John Wiley & Sons, Inc., New York, N.Y. (1954), and A. Williams, Flame Retardant Coatings and Building Materials, Noyes Data Corp., Park Ridge (N.J.) (1974), all of said publications being incorporated herein in toto by reference.

In addition to the above described methods for protecting a substrate from heat and fire by applying the intumescent agents of formula I via a intumescent coating composition to a desired substrate, it is also within the scope of this invention to protect said substrates by applying the intumescent agents of formula I directly to the desired substrate in any suitable manner, e.g., electrodeposition, spraying of powder intumescent agent onto an adhesive substrate, etc. The amount of intumescent agent which can be directly applied to any particular substrate is determined solely by balancing the degree of protection desired, the economics of the situation, etc.

The intumescent agents of this invention are efficient, have excellent hydrolytic stability, and intumesce without flaming to form foams having good volume, cell structure, and adherence to substrates, such as wood, metal, and plastics. They are also useful as flame retardants in normally flammable compositions.

The following examples are provided for the purpose of further illustration only and are not intended to be limitations on the disclosed invention. Unless otherwise specified, all temperatures are expressed in degrees centigrade; all weights are expressed in grams; and all volumes are expressed in milliliters.

EXAMPLE 1

A quantity of 29.7 grams of 3,9-dichloro-2,4,8,10-tetraoxa-3,9-diphosphaspiro(5.5)undecane-3,9-dioxide, 43.6 grams of 2,3-dibromopropanol and 0.1 gram of magnesium oxide were mixed together and heated to 110° C. to drive off the hydrogen chloride as it evolved. Hydrogen chloride evolution stopped after about 2 hours, at which time the reaction mixture was permitted to cool to room temperature. The resultant viscous product was washed with ammonium hydroxide at 60° C. and then with water. The light brown viscous liquid was dried under vacuum. Percent bromine calculated for 3,9-bis(2,3,-dibromopropoxy)-2,4,8,10-tetraoxa-3,9-diphosphaspiro(5.5)undecane-3,9-dioxide is 48.5%. Percent bromine found by elemental analysis was 47.7%.

EXAMPLE 2

Dibromopentaerythritol cyclic chlorophosphite,

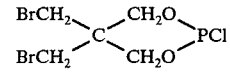

was prepared by reacting dibromopentaerythritol with a slight molar excess of phosphorus trichloride.

The above chlorophosphite, 380 grams, was then reacted with a slight molar excess of gaseous chlorine, 95 grams, in the presence of 200 ml. of methylene dichloride. An ice bath was used during the chlorine addition to hold the reaction temperature to 25° to 30° C. After the chlorine addition was complete, the methylene dichloride was evaporated, leaving the product, 2,2-di(bromomethyl)-3-chloropropyl dichlorophosphate,

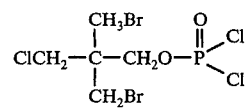

A quantity of 279 grams (0.7 mole) of the above dichlorophosphate was mixed with 47.7 grams (0.35 mole) of pentaerythritol in the presence of 300 ml. of toluene and 0.5 gram of magnesium oxide. The reaction mixture was heated to reflux temperature to remove hydrogen chloride. After about 12 hours at reflux temperature, the mixture was allowed to cool and was subjected to vacuum to remove additional hydrogen chloride. The white precipitate was filtered and washed once with ammonium hydroxide and twice with water, and then crystallized from methanol. The product was identified as 3,9-bis(2,2-di(bromomethyl)-3-chloropropoxy)-2,4,8,10-tetraoxa-3,9-diphosphaspiro(5.5)undecane-3,9-dioxide. Melting point was 212° C. Calculated halogen content is Br, 40.7%; Cl, 8.93%; found Br, 41.1%; Cl, 9.12%.

EXAMPLE 3

To a suspension of 29.7 grams (0.1 mole) of 3,9-dichloro-2,4,8,10-tetraoxa-3,9-diphosphaspiro(5.5)undecane-3,9-dioxide in 250 ml. of benzene was added 30 grams of diethylamine in 50 ml. of benzene. The mixture was heated to reflux temperature for 3 hours and then filtered to remove the precipitated amine hydrochloride. Upon evaporation of the benzene, a clear oil remained which crystallized upon cooling, and was subsequently recrystallized with water. Melting point of the white crystalline product was 189.5° to 190.5° C. Calculated elemental analysis for 3,9-bis(N,N-diethylamino)-2,4,8,10-tetraoxa-3,9-diphosphaspiro(5.5)undecane-3,9-dioxide was C, 42.2%; H, 7.6%; N, 7.6%; N, 7.6%. Found: C, 41.1%; H, 7.5%; N, 7.2%.

EXAMPLE 4

Preparation of 3,9-bis(2,2-(dimethyl)-3-chloropropoxy)-2,4,8,10-tetraoxa-3,9-diphosphaspiro(5.5)undecane-3,9-dioxide.

A quantity of 2,2-dimethyl-3-chloropropyl dichlorophosphate (748.2 gm; 3 moles) was dissolved in 800 ml. of toluene. To the above was added 209 gm (1.5 moles)

of pentaerythritol and 3 gm of magnesium oxide. The solution was refluxed at 110° C. for 9 hours. The mixture was filtered leaving a white solid. This material was washed with 1 liter of acetone, followed by a wash with an aqueous ammonia solution having a pH of from about 8 to about 9. This solution was filtered and washed with 2 liters of water followed by a final acetone wash of 1 liter. The material was dried in a forced air oven at 105° C. for 3½ hours. About 442 gm of material was recovered giving a yield of about 63%. The melting point of the compound was determined to be 282° to 285° C.

EXAMPLE 5

Preparation of 3,9-bis(2,2-(dibromomethyl)-3-bromopropoxy)-2,4,8,10-tetraoxa-3,9-diphosphaspiro(5.5undecane-3,9-dioxide.

A quantity of phosphoryl chloride (50 gm) and 0.4 gm of magnesium oxide were heated to 85° C. Tribromoneopentyl alcohol (300 gm; 0.924 moles) were added in increments over a 1.25 hour period. The reaction continued at a temperature of 85° C. for 6 hours. The excess phosphoryl chloride was distilled under an aspirator vacuum to a pot temperature of 130° C. The reaction was cooled to 100° C. and 0.462 mole (62.8 gm) of pentaerythritol and 300 ml. of toluene were added. Additional toluene was added as needed. The system was refluxed for 6½ hours, cooled to room temperature, filtered, and dried at 100° C. in a vented oven.

A residue was washed with about 1 liter of water. An aqueous ammonia solution was added to give a pH of about 8. The residue was then washed with water and then with acetone and finally dried at 100° C. in air vented oven. Yield: 335 gm (83%); Melting point: 225° to 228° C.

EXAMPLE 6

Preparation of 3,9-bis(2,2-(dichloromethyl)-3-chloropropoxy)-2,4,8,10-tetraoxa-3,9-diphosphaspiro (5.5)undecane-3,9-dioxide.

About 1 mole of 2,2-dichloromethyl-3-chloropropyl dichlorophosphate was placed into a 3-liter flask. To this was added 1 gm of magnesium oxide, 2 liters of toluene, and 0.5 mole of pentaerythritol. The reaction was stirred and heated at reflux until the acid number was less than 10. The toluene was stripped off and the solid portion was placed in an oven and dried without being washed. The product was ground up after having been dried for 4 hours at 110° C. and washed with a 50/50 acetone/water solution. The resulting product had a melting point of 197° to 200° C. and the melt remained clear until decomposition was reached at 270° to 280° C.

EXAMPLE 7

A small amount of 3,9-bis(2,2-(dibromethyl)-3-bromopropoxy)-2,4,8,10-tetraoxa-3,9-diphosphaspiro(5.5)undecane-3,9-dioxide was placed on an aluminum spatula and flamed with a propane torch. The compound intumesced without exhibiting any flame to form an excellent volume of foam having a good cell structure.

Example 7 was repeated using 3,9-bis(N,N-diethylamino)-2,4,8,10-tetraoxa-3,9-diphosphaspiro(5.5)undecane-3,9-dioxide, 3,9-bis(2,3-dibromopropoxy)-2,4,8,10-tetraoxa-3,9-diphosphaspiro(5.5)undecane-3,9-dioxide, 3,9-bis(2,2-(dibromomethyl)-3-chloropropoxy)-2,4,8,10-tetraoxa-3,9-diphosphaspiro(5.5)undecane-3,9-dioxide, 3,9-bis(2,2,-(dimethyl)-3-chloropropoxy)-2,4,8,10-tetraoxa-3,9-diphosphaspiro(5.5) undecane-3,9-dioxide, 3,9-bis(2,2-dimethylpropoxy)-2,4,8,10-tetraoxa-3,9-diphosphaspiro(5.5)undecane-3,9-dioxide, and 3,9-bis(2,2-(dichloromethyl)-3-chloropropoxy)-2,4,8,10-tetraoxa-3,9-diphosphaspiro(5.5)undecane-3,9-dioxide, and all of the above compounds intumesce without exhibiting any flame to form an excellent volume of foam having a good cell structure.

As with the above, compounds, other intumescent agents within the scope of formula I of this invention, for example, 3,9-bis(2,2-(dimethyl)-3-bromopropoxy)-2,4,8,10-tetraoxa-3,9-diphosphaspiro(5.5) undecane-3,9-dioxide, 3,9-bis(2,2-(dichloromethyl)-3-bromopropoxy)-2,4,8,10-tetraoxa-3,9diphosphaspiro(5.5)undecane-3,9-dioxide, 3,9-dimethyloxy-2,4,8,10-tetraoxa-3,9-diphosphaspiro(5.5)undecane-3,9-dioxide, 3,9-bis(2,3-dichloropropoxy)-2,4,8,10-tetraoxa-3,9-diphosphaspiro(5.5)undecane-3,9-dioxide, 3,9-bis(2-chloroethoxy)-2,4,8,10-tetraoxa-3,9-diphosphaspiro(5.5)undecane-3,9-dioxide, 3,9-di-n-propoxy-2,4,8,10-tetraoxa-3,9-diphosphaspiro(5.5)undecane-3,9-dioxide, 3,9-bis(N,N-dimethylamino)-2,4,8,10-tetraoxa-3,9-diphosphaspiro(5.5)undecane-3,9-dioxide, and 3,9-diamino-2,4,8,10-tetraoxa-3,9-diphosphaspiro(5.5)undecane-3,9-dioxide, will, when subjected to a heat source such as that employed in Example 7, intumesce without exhibiting any flame to form an excellent volume of foam having a good cell structure.

EXAMPLE 8

Sears Latex Semi Gloss (30) 77865 tint base brand paint (75 grams; Sears, Roebuck & Co., Chicago, Ill.), 5 grams of a resinous chlorinated paraffin (Chlorowax ® 70 brand resinous chlorinated paraffin Diamond Alkali Co., Cleveland, OH), and 75 grams of the intumescent agent of Example 3 were mixed using a high shear mixer. Water (roughly 10 grams) was added during the mixing procedure to maintain a good mixing viscosity. The mixing was continued until the mixture displayed uniform appearance.

The above prepared intumescent coating composition was applied to a fiberboard substrate and allowed to dry. After the intumescent coating composition was dry and tack free it was exposed to a propane torch whereupon said intumescent coating composition enlarged, swelled, and bubbled up to form a insulative coating protecting the fiberboard substrate from the fire and heat of the propane torch.

Example 8 clearly demonstrates that the intumescent-coating compositions within the scope of this invention when applied to a desired substrate will protect said substrate from heat and fire.

Exemplary of other intumescent agents within the scope of formula I which, when incorporated into the intumescent coating compositions of this invention, also protect a substrate from heat and fire include 3,9-bis(2,2-dibromomethyl)-3-bromopropoxy)-2,4,8,10-tetraoxa-3,9-diphosphaspiro(5.5)undecane-3,9-dioxide, 3,9-bis-(2,2-(dichloromethyl)-3-chloropropoxy)-2,4,8,10-tetraoxa-3,9-diphosphaspiro(5.5)undecane-3,9-dioxide, 3,9-bis(2,2-(dimethyl)-3-chloropropoxy)-2,4,8,10-tetraoxa-3,9-diphosphaspiro(5.5)undecane-3,9-dioxide, 3,9-bis(2,2-(dimethyl)-3-bromopropoxy)-2,4,8,10-tetraoxa-3,9-diphosphaspiro(5.5)undecane-3,9-dioxide, 3,9-bis-(2,2-(dibromomethyl)-3-chloropropoxy)-2,4,8,10-tetraoxa-3,9-diphosphaspiro(5.5)undecane-3,9-dioxide, 3,9-bis(2,2-(dichloromethyl)-3-bromopropoxy)-2,4,8,10-tetraoxa-3,9-diphosphaspiro(5.5)undecane-3,9-dioxide, 3,9-bis(2,2-dimethylpropoxy)-2,4,8,10-tetraoxa-3,9-diphosphaspiro(5.5)undecane-3,9-dioxide, 3,9-dimethyloxy-2,4,8,10-tetraoxa-3,9-diphosphaspiro(5.5)undecane-3,9-dioxide, 3,9-bis(2,3-dibromopropoxy)-2,4,8,10-tetraoxa-3,9-diphosphaspiro(5.5)undecane-3,9-dioxide, 3,9-bis(2,3-dicloropropoxy)-2,4,8,10-tetraoxa-3,9-diphosphaspiro(5.5)undecane-3,9-dioxide, 3,9-bis(2-chloroethoxy)-2,4,8.10-tetraoxa-3,9-diphosphaspiro(5.5)undecane-3,9-dioxide, 3,9-di-n-propoxy-2,4,8,10-tetraoxa-3,9-diphosphaspiro(5.5)undecane-3,9-dioxide, 3,9-bis(N,N-dimethylamino)-2,4,8,10-tetraoxa-3,9-diphosphaspiro(5.5)undecane-3,9-dioxide, and 3,9-diamino-2,4,8,10-tetraoxa-3,9-diphosphaspiro(5.5)undecane-3,9-dioxide.

Alternatively, when the intumescent agents within the scope of formula I, as exemplified by the above list of compounds, are applied directly to a substrate surface in any suitable manner, e.g., electrodeposition, spraying of powder intumescent agent onto an adhesive substrate, etc., said intumescent agents will protect said substrate from heat and fire.

The embodiments of the invention in which an exclusive property or privilege is claimed are defined as follows:

1. An intumescent composition comprising a coating vehicle and an intumescing amount of an intumescent agent of the formula

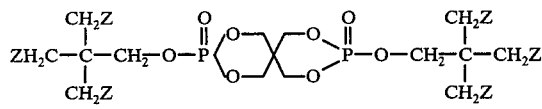

wherein each Z is independently selected from the group consisting of hydrogen and halogen.

2. The intumescent composition according to claim 1, wherein each Z is independently selected from the group consisting of hydrogen, chlorine, and bromine.

3. The intumescent composition according to claim 2, wherein at least one Z is selected from the group consisting of chlorine and bromine.

4. The intumescent composition according to claim 1, wherein said non-flamming intumescent agent is selected from the group consisting of 3,9-bis(2,2-(dibromomethyl)-3-bromopropoxy)-2,4,8,10-tetroaxa-3,9-diphosphaspiro(5.5)undecane-3,9-dioxide, 3,9-bis-(2,2-(dichloromethyl)-3-chloropropoxy)-2,4,8,10-tetraoxa-3,9-diphosphaspiro (5.5)undecane-3,9-dioxide, 3,9-bis(2,2-(dimethyl)-3-chloropropoxy)-2,4,8,10-tetraoxa-3,9-diphosphaspiro (6.6)undecane-3,9-dioxide,3,9-bis(2,2-(dimethyl)-3-bromopropoxy-2,4,8,10-tetraoxa-3,9-diphosphaspiro(5.5)undecane-3,9-dioxide, 3,9-bis(2,2-(dibromomethyl)-3-chloropropoxy)-2,4,8,10-tetraoxa-3,9-diphosphaspiro(5.5)undecane-3,9-dioxide, 3,9-bis(2,2-(dichloromethyl)3-bromopropoxy)-2,4,8,10-tetraoxa-3,9-diphosphaspiro(5.5)undecane-3,9-dioxide.

5. A method of protecting a substrate from heat and fire comprising applying to said substrate an intumescing amount of an intumescent agent of the formula

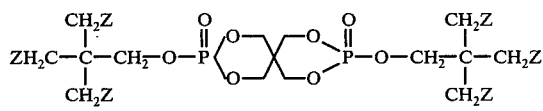

wherein each Z is independently selected from the group consisting of hydrogen and halogen.

6. The composition of claim 1, wherein said coating vehicle is paint.

7. The composition of claim 1 wherein said coating vehicle is varnish.

8. The composition of claim 1 wherein said coating vehicle is lacquer.

9. A shaped substantially flammable article having disposed on the surface thereof a non-flaming intumescent topical coating composition for protecting said article from heat and fire comprising a coating vehicle and an intumescing amount of the non-flaming intumescent agent described in claim 1.

* * * * *